United States Patent [19]
Bok et al.

[11] Patent Number: 6,165,984
[45] Date of Patent: Dec. 26, 2000

[54] NARINGIN AND NARINGENIN AS INHIBITORS OF ACYL COA-CHOLESTEROL-O-ACYLTRANSFERASE

[75] Inventors: Song-Hae Bok; Tae-Sook Jeong; Ki-Hwan Bae, all of Daejeon; Yong-Bok Park; Myung-Sook Choi, both of Daegu; Surk-Sik Moon, Chungcheongnam-do; Yong-Kook Kwon, Daejeon; Eun-Sook Lee, Daejeon; Byung-Hwa Hyun, Daejeon; Yang-Kyu Choi, Daejeon; Chul-Ho Lee, Daejeon; Jun-Sung Lee, Daejeon; Kwang-Hee Son, Daejeon; Byoung-Mog Kwon, Daejeon; Young-Kook Kim, Daejeon; Doil Choi, Daejeon; Sung-Uk Kim, Daejeon; Ingyu Hwang, Daejeon; Jung-Ah Ahn, Daejeon; Young-Bae Park, Seoul; Hyo-Soo Kim, Seoul; Seong-Choon Choe, Seoul, all of Rep. of Korea

[73] Assignee: Korea Institute of Science & Technology, Seoul, Rep. of Korea

[21] Appl. No.: 09/181,393

[22] Filed: Oct. 28, 1998

[30] Foreign Application Priority Data

| Oct. 28, 1997 | [KR] | Rep. of Korea | 97-55579 |
| Mar. 28, 1998 | [KR] | Rep. of Korea | 98-10889 |
| Apr. 1, 1998 | [KR] | Rep. of Korea | 98-11450 |
| Apr. 8, 1998 | [KR] | Rep. of Korea | 98-12411 |
| Apr. 14, 1998 | [KR] | Rep. of Korea | 98-13283 |

[51] Int. Cl.$^7$ .......................... A61K 31/70; A61K 31/35; A61K 47/00
[52] U.S. Cl. .......................... 514/27; 514/453; 514/456; 424/439
[58] Field of Search .......................... 514/27, 453, 456; 424/439

[56] References Cited

U.S. PATENT DOCUMENTS

| 5,145,839 | 9/1992 | Beljanski | 514/27 |
| 5,679,703 | 10/1997 | Yanase et al. | 514/431 |
| 5,807,860 | 9/1998 | Inoue et al. | 514/255 |
| 5,877,208 | 3/1999 | Bok et al. | 514/456 |

FOREIGN PATENT DOCUMENTS

| 82-80358 | 10/1996 | Japan. |
| 82-83154 | 10/1996 | Japan. |

*Primary Examiner*—Kathleen K. Fonda
*Attorney, Agent, or Firm*—Anderson Kill & Olick, P.C.

[57] ABSTRACT

Methods for inhibiting the activity of acyl CoA-cholesterol-o-acyltransferase, inhibiting the accumulation of macrophage-lipid complex on the arterial endothelium, and preventing or treating hepatic diseases in a mammal comprise administering naringin or naringenin thereto.

10 Claims, 6 Drawing Sheets

NARINGIN AND NARINGENIN AS INHIBITORS OF ACYL COA-CHOLESTEROL-O-ACYLTRANSFERASE

FIELD OF THE INVENTION

The present invention relates to methods for inhibiting the activity of acyl CoA-cholesterol-o-acyltransferase (ACAT), inhibiting the accumulation of macrophage-lipid complex on the arterial endothelium, and preventing or treating hepatic diseases in a mammal, said methods comprising administering naringin or naringenin to the mammal.

BACKGROUND OF THE INVENTION

In recent years, coronary cardio-circulary diseases, e.g., atherosclerosis and hypercholesterolemia, have increasingly become a major cause of deaths. It has been reported that an elevated plasma cholesterol level causes the deposition of fat, macrophages and foam cells on the wall of blood vessels, such deposit leading to plaque formation and then to atherosclerosis (Ross, R., *Nature,* 362, 801–809(1993)). One of the methods for decreasing the plasma cholesterol level is alimentotherapy to reduce the ingestion of cholesterol and lipids. Another method is to inhibit the absorption of cholesterol by inhibiting enzymes involved therein.

Acyl CoA-cholesterol-o-acyltransferase (ACAT) promotes the esterification of cholesterol in blood. Foam cells are formed by the action of ACAT and contain a large amount of cholesterol ester carried by low density lipoproteins. The formation of foam cells on the wall of artery increases with the ACAT activity, and, accordingly, an inhibitor of ACAT may also be an agent for preventing atherosclerosis. Further, it has been reported that the blood level of LDL-cholesterol can be reduced by inhibiting the ACAT activity (Witiak, D. T. and D. R. Feller (eds.), *Anti-Lipidemic Drugs: Medicinal, Chemical and Biochemical Aspects,* Elsevier, pp159–195(1991)).

On the other hand, deterioration of hepatic functions may occur due to an excessive intake of alcohol or foods having a high lipid content, or an infection of hepatitis B or C virus, and it may develop into hepatitis, hepatocirrhosis or hepatic cancer. In particular, the excessive intake of fat-containing foods and alcohol causes fatty liver wherein a large amount of lipids is deposited in the liver tissue and the levels of serum GOT (glutamate-oxaloacetate transaminase), GPT (glutamate-pyruvate transaminase) and γ-GTP (γ-glutamyl transpeptidase) are elevated (T. Banciu et al., *Med. Interne.,* 20, 69–71(1982); and A. Par et al., *Acta. Med. Acad. Sci. Hung.,* 33, 309–319(1976)).

Numerous efforts have been made to develop medicines which inhibit ACAT activity; and, as a result, several compounds isolated from the cultures of various microorganisms have been reported. Examples of such compounds include pyripyropenes isolated from the culture of *Aspergillus fumigatus* (S. Omura et al., *J. Antibiotics,* 46, 1168–1169(1993)) and Acaterin isolated from Pseudomonas sp. (S. Nagamura et al., *J. Antibiotics,* 45, 1216–1221(1992)).

Further, as a treating agent for hypercholesterolemia, a HMG-CoA reductase inhibitor named Lovastatin® has been developed and marketed by Merck Co., U.S.A. However, this medicine is known to induce adverse side effect of increasing creatin kinase in the liver.

Accordingly, there has continued to exist a need to develop non-toxic inhibitors of ACAT and macrophage-lipid complex accumulation on the arterial epithelium, and a preventive or treating agent for the hepatic diseases.

The present inventors have endeavored to develop a novel and potent ACAT inhibitor, macrophage-lipid complex accumulation inhibitor and treating agent for the hepatic diseases from natural materials, and, as a result, have discovered that naringin or naringenin has a potent ACAT inhibitory activity, macrophage-lipid complex accumulation inhibitory activity, and preventive or treating activity on the hepatic diseases.

Naringin ($C_{27}H_{32}O_{14}$, M.W.: 580.53) and the aglycon of naringin, naringenin ($C_{15}H_{12}O_5$, M.W.: 272.25), are flavonoids found in lemons, grapefruits, tangerines, citrons and oranges (*Citrus sinensis*) (Horowitz, Gentili, *Tetrahedron,* 19, 773(1963)).

It has been reported that naringin or naringenin has anti-cancer, anti-viral and cholesterol lowering activities (Monforte, M. T., et al., *Farmaco.,* 50(9), 595–599 (September 1995); JP 95-86929; JP 95-86930; Felica, V., et al., *J. Med. Virol.,* 15, 71–79(1985); EP 0352147 A2(1990.1.24); and Martin, M. J., et al., *Pharmacol.,* 49, 144–150(1994)).

Further, naringin has been used as a bitter tasting agent, sweetener or chewing gum base.

However, hitherto, none of the ACAT inhibitory activity, macrophage-lipid complex accumulation inhibitory activity and preventive or treating activity on the hepatic diseases of naringin or naringenin has been reported.

SUMMARY OF THE INVENTION

Accordingly, it is an object of the present invention to provide a method for inhibiting the ACAT activity in a mammal.

Another object of the present invention is to provide a method for inhibiting the accumulation of macrophage-lipid complex on the endothelial wall of an artery in a mammal.

A further object of the present invention is to provide a method for preventing or treating hepatic diseases in a mammal.

BRIEF DESCRIPTION OF THE DRAWINGS

The above and other objects and features of the present invention will become apparent from the following description of the invention, when taken in conjunction with the accompanying drawings, in which:

FIGS. 1A, 1B and 1C show the arteries of the rabbits administered with 1% cholesterol; 1% cholesterol plus 1 mg/kg Lovastatin®; and 1% cholesterol plus 0.1% naringin, respectively.

DETAILED DESCRIPTION OF THE INVENTION

In accordance with one aspect of the present invention, there is provided a method for inhibiting the acyl-CoA cholesterol-o-acyltransferase (ACAT) activity in a mammal which comprises administering naringin or naringenin thereto.

In accordance with another aspect of the present invention, there is provided a method for inhibiting the accumulation of macrophage-lipid complex on the endothelial wall of an artery in a mammal which comprises administering naringin or naringenin thereto.

In accordance with a further aspect of the present invention, there is provided a method for preventing or treating hepatic diseases in a mammal which comprises administering naringin or naringenin thereto.

Naringin and naringenin may be extracted from the peel of citrus or synthesized according to the process described by Zemplen, Bognar, Ber., 75, 1043(1943) and Seka, Prosche, Monatsh., 69, 284(1936). Further, naringenin can be prepared by the hydrolysis of naringin.

Naringin or naringenin exerts an inhibitory effect on the ACAT activity and the accumulation of macrophage-lipid complex on the endothelial wall of an artery, and a preventive or treating effect on hepatic diseases at a dose of 0.1 mg/kg/day or more, the inhibitory effect increasing with the dose thereof.

Moreover, in spite of its potent efficacies, naringin or naringenin shows little toxicity or mitogenicity in tests using mice. More specifically, naringin or naringenin exhibits no toxicity when it is orally administered to a mouse at a dose of 1,000 mg/kg, which corresponds to an oral administration dose of 50 to 100 g/kg body weight of naringin or naringenin for a person weighing 50 kg. Further, naringin and naringenin exert no adverse effects on the liver function.

The present invention also provides a pharmaceutical composition for inhibiting the ACAT activity and accumulation of macrophage-lipid complex on the endothelial wall of an artery, and for preventing or treating hepatic diseases, which comprise naringin or naringenin as an active ingredient and pharmaceutically acceptable excipients, carriers or diluents.

A pharmaceutical formulation may be prepared in accordance with any of the conventional procedures. In preparing the formulation, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical composition of the present invention can be administered via various routes including oral, transdermal, subcutaneous, intravenous and intramuscular introduction. In case of human, a typical daily dose of naringin or naringenin may range from about 0.1 to 100 mg/kg body weight, preferably 3 to 10 mg/kg body weight, and can be administered in a single dose or in divided doses.

However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

Moreover, naringin or naringenin can be incorporated in foods or beverages, as an additive or a dietary supplement, for the purpose of inhibiting the ACAT activity, inhibiting the accumulation of macrophage-lipid complex on the arterial endothelium and/or preventing or treating hepatic diseases. The foods or beverages may include meats; juices such as a vegetable juice (e.g., carrot juice and tomato juice) and a fruit juice (e.g., orange juice, grape juice, pineapple juice, apple juice and banana juice); chocolates; snacks; confectionery; pizza; foods made from cereal flour such as breads, cakes, crackers, cookies, biscuits, noodles and the likes; gums; dairy products such as milk, cheese, yogurt and ice creams; soups; broths; pastes, ketchups and sauces; teas; alcoholic beverages; carbonated beverages such as Coca-Cola® and Pepsi-Cola®; vitamin complexes; and various health foods.

In this case, the content of naringin or naringenin in a food or beverage may range from 0.01 to 5% by weight. In particular, the beverage according to the present invention may comprise 200 to 10,000 mg of naringin or naringenin per 1000 ml of the beverage.

As described above, naringin or naringenin can be used as an effective, non-toxic pharmaceutical agent for inhibiting ACAT activity, inhibiting the accumulation of macrophage-lipid complex on the arterial endothelium, and/or preventing or treating hepatic diseases.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

EXAMPLE 1

Extraction of Naringin from Citrus Peel

The peels of tangerines (Cheju Island, Korea), citrons (Jeollanamdo, Korea), and oranges, grapefruits and lemons (California, California, U.S.A.) were dried at a room temperature and powdered to a particle size ranging from 100 to 200 μm. 50 ml of methanol was added to 500 mg each of the citrus peel powder and extracted in a water bath at 50° C. for 6 hours. The extract thus obtained was cooled and filtered, and then methanol was added to the filtrate to a volume of 50 ml.

To confirm the content of naringin in the extract obtained above, 5.0 μl of the resulting extract was subjected to high performance liquid chromatography (HPLC) using Lichrosorb RP-8 column (5 μm, 4×250 mm) which was pre-equilibrated with 37% methanol and maintained at a temperature of 30° C. The extract was eluted with 37% methanol at a flow rate of 1.0 ml/min. Standard solutions were prepared by dissolving naringin (Sigma Chemical Co. U.S.A.) in methanol to final concentrations of 0.1, 0.2, 0.3, 0.4 and 0.5 mg/ml, and subjected to HPLC under the same condition as above. The eluates were detected at 280 nm with UV-VIS spectrophotometer and the content of naringin was calculated by comparing the areas of HPLC profiles of the citrus peel extract and the standard solution. The content (%) of naringin in various citrus peel extracts is shown in Table 1.

TABLE I

| | Naringin (%) |
|---|---|
| Orange | trace amount |
| Lemon | trace amount |
| Tangerine | trace amount |
| grapefruit | 4.70 |
| citron | 0.80 |

EXAMPLE 2

Toxicity of Orally Administered Naringin or Naringenin 7 to 8 week-old, specific pathogen-free ICR female mice (6 heads) each weighing about 25 to 29 g and male mice (6 heads) each weighing about 34 to 38 g were bred under a condition of temperature 22±1° C., moisture 55±5% and photoperiod 12L/12D. Fodder (Cheiljedang Co., mouse and rat fodder) and water were sterilized and fed to the mice.

Naringin or naringenin was dissolved in 0.5% Tween 80 to a concentration of 100 mg/ml, and the solution was orally administered to the mice in an amount of 0.2 ml per 20 g of mouse body weight. The solution was administered once and the mice were observed for 10 days for signs of adverse effects or death according to the following schedule: 1, 4, 8, and 12 hours after the administration and, every 12 hours thereafter. The weight changes of the mice were recorded every day to examine the effect of naringin or naringenin. Further, on the 10th day, the mice were sacrificed and the internal organs were visually examined.

All the mice were alive at day 10 and naringin or naringenin showed no toxicity at a dose of 1,000 mg/kg. The autopsy revealed that the mice did not develop any pathological abnormality, and no weight loss was observed during the 10 day test period. Accordingly, it was concluded that naringin or naringenin is not toxic when orally administered to an animal.

EXAMPLE 3

Administration of Naringin or Naringenin to an Animal 30 four-week-old Sprague-Dawley rats (Taihan laboratory animal center, Korea) each weighing about 90 to 110 g were evenly divided into three dietary groups by a randomized block design. The rats of the three groups were fed with three different high-cholesterol diets, i.e., AIN-76 laboratory animal diet (ICN Biochemicals, Cleveland, Ohio, U.S.A.) containing 1% cholesterol (Control group), and 1% cholesterol plus 0.1% naringin or naringenin, respectively. The compositions of diets fed to the three groups are shown in Table II.

TABLE II

| Dietary group Ingredients | Control group | Naringin group | Naringenin group |
|---|---|---|---|
| Casein | 20 | 20 | 20 |
| D,L-methionine | 0.3 | 0.3 | 0.3 |
| Corn starch | 15 | 15 | 15 |
| Sucrose | 49 | 48.9 | 48.9 |
| Cellulose powder[*1] | 5 | 5 | 5 |
| Mineral mixture[*1] | 3.5 | 3.5 | 3.5 |
| Vitamin mixture[*1] | 1 | 1 | 1 |
| Choline bitartrate | 0.2 | 0.2 | 0.2 |
| Corn oil | 5 | 5 | 5 |
| Cholesterol | 1 | 1 | 1 |
| Naringin[*2] | — | 0.1 | — |
| Naringenin[*2] | — | — | 0.1 |
| Total | 100 | 100 | 100 |

[*1]Purchased from TEKLAD premier Co. (Madison, WI, U.S.A.)
[*2]Purchased from Sigma Chemical Co. (St. Louis, Mo, U.S.A.)

The rats were allowed to feed freely on the specified diet together with water for six weeks, the ingestion amount was recorded daily and the rats were weighed every 7 days, and then the record was analyzed. All rats showed a normal growth rate and there was observed no significant difference among the three groups in terms of the feed ingestion amount and the weight gain.

EXAMPLE 4

Determination of Total Cholesterol, HDL-Cholesterol and Neutral Lipid Content in Plasma The effect of administering naringin or naringenin to rats on the plasma cholesterol and neutral lipid content was determined as follows.

Blood samples were taken from the rats of the three dietary groups and plasma HDL fractions were separated therefrom by using HDL-cholesterol reagent (Sigma Chemical Co., Cat. No. 352-3) containing dextran-sulfate. Total cholesterol and HDL-cholesterol levels were determined by using Sigma Diagnostic Kit Cat. No. 352-100(Sigma Chemical Co., U.S.A.) (Allain et al., *Clin. Chem.*, 20, 470–475(1974)). Neutral lipid level was determined by using Sigma Diagnostic Kit Cat. No. 339-50(Bucolo, G. and David, H., *Clin. Chem.*, 19, 476–482(1973)). The result is shown in Table III, wherein the total plasma cholesterol levels in naringin and naringenin-fed rat groups decreased by 32% and 18%, respectively, as compared with that of the control group.

TABLE III

| Group Lipid Conc. | Control group | Naringin group | Naringenin group |
|---|---|---|---|
| Total-C (mg/dl) | 147.8 ± 34.8 | 100.8 ± 16.1 | 120.9 ± 25.9 |
| HDL-C (mg/dl) | 22.2 | 24.0 | 23.4 |
| $\frac{\text{HDL-C}}{\text{Total-C}}$ (%) | 15.7 ± 5.3 | 23.9 ± 7.6 | 20.8 ± 9.1 |
| TG (mg/dl) | 99.2 ± 18.9 | 86.7 ± 14.6 | 103.4 ± 18.2 |

*Total-C: Total-cholesterol
*HDL-C: HDL-cholesterol
*TG: Triglyceride

EXAMPLE 5

Activity of Naringin and Naringenin in ACAT Inhibition (Step 1) Preparation of Microsomes To determine the effects of naringin and naringenin feeding to rats on the activity of ACAT, microsomes were separated from the liver tissue to be used as an enzyme source.

First, the rats of the three groups prepared in Example 3 were sacrificed by decapitation and the livers were excised. 1 g each of the livers was homogenized in 5 ml of homogenization medium (0.1 M $KH_2PO_4$, pH 7.4, 0.1 mM EDTA and 10 mM β-mercaptoethanol). The homogenate was centrifuged at 3,000×g for 10 min. at 4° C. and the supernatant thus obtained was centrifuged at 15,000×g for 15 min. at 4° C. to obtain a supernatant. The supernatant was put into an ultracentrifuge tube (Beckman) and centrifuged at 100,000×g for 1 hour at 4° C. to obtain microsomal pellets, which were then suspended in 3 ml of the homogenization medium and centrifuged at 100,000×g for 1 hour at 4° C. The pellets thus obtained were suspended in 1 ml of the homogenization medium. The concentration of proteins in the resulting suspension was determined by Lowry's method and then adjusted to 4 to 8 mg/ml. The resulting suspension was stored in a deep freezer (Biofreezer, Forma Scientific Inc.).

(Step 2) ACAT Assay 6.67 μl of 1 mg/ml cholesterol solution in acetone was mixed with 6 μl of 10% Triton WR-1339(Sigma Co.) in acetone and, then, acetone was removed from the mixture by evaporation using nitrogen gas. Distilled water was added to the resulting mixture in an amount to adjust the concentration of cholesterol to 30 mg/ml.

To 10 μl of the resulting aqueous cholesterol solution were added 10 μl of 1 M $KH_2PO_4$(pH 7.4), 5 μl of 0.6 mM bovine serum albumin (BSA), 10 μl of microsome solution obtained in (Step 1) and 55 μl of distilled water (total 90 μl). The mixture was pre-incubated in a waterbath at 37° C. for 30 min.

10 μl of (1-$^{14}$C) oleoyl-CoA solution (0.05 μCi, final concentration: 10 μM) was added to the pre-incubated mixture and the resulting mixture was incubated in a waterbath at 37° C. for 30 min. To the mixture were added 500 μl of isopropanol:heptane mixture (4:1(v/v)) 300 μl of heptane and 200 μl of 0.1 M $KH_2PO_4$(pH 7.4), and the mixture was mixed violently by using a vortex and then allowed to stand at a room temperature for 2 min.

200 μl of the resulting supernatant was put in a scintillation bottle and 4 ml of scintillation fluid (Lumac) was added thereto. The mixture was assayed for radioactivity with 1450 Microbeta liquid scintillation counter (Wallacoy, Finland). ACAT activity was calculated as picomoles of cholesteryl oleate synthesized per min. per mg protein (pmoles/min/mg protein). The result is shown in Table IV.

TABLE IV

| Group | ACAT activity (pmole/min/mg protein) | % Inhibition on ACAT activity |
| --- | --- | --- |
| Control group | 806.2 ± 105.2 | 0 |
| 0.1% naringin group | 643.5 ± 80.7 | 20.2 |
| 0.1% naringenin group | 666.3 ± 65.3 | 17.4 |

As can be seen from Table IV, ACAT activities observed in naringin and naringenin-fed rat groups are lower than that of the control group by 20.2% and 17.4%, respectively.

EXAMPLE 6

Inhibition of Plaque Formation Caused by Macrophage-Lipid Complex in Naringin and Naringenin-Fed Animals (Step 1) Administration of Naringin and Naringenin to Animals 24 three-month-old New Zealand White rabbits (Yeonam Horticulture and Animal Husbandry College, Korea) each weighing about 2.5 to 2.6 kg were bred under a condition of temperature 20±2° C., relative humidity 55±5%, and photoperiod 12L/12D. The rabbits were divided by a group of 6 rabbits, and the rats of four groups were fed with four different diets, i.e., RC4 diet (Oriental Yeast Co., Japan) containing 1% cholesterol (Control group); 1% cholesterol plus 1 mg/kg Lovastatin® (Merck, U.S.A.) (Comparative group); 1% cholesterol plus 0.1% naringin; and 1% cholesterol plus 0.1% naringenin, respectively. RC4 diet comprises 7.6% moisture, 22.8% crude protein, 2.8% crude fat, 8.8% crude ash, 14.4% crude cellulose and 43.6% soluble nitrogen-free substances. The rabbits were bred for 6 weeks while being allowed free access to the diets and water.

(Step 2) Analysis for Fatty Streak in the Main Artery

The rabbits bred in (Step 1) were sacrificed and their chest were incised. The main artery was cut out therefrom in a length of about 5 cm downward from the site 1 cm above the aortic valve and the fat surrounding the main artery was removed. The main artery was incised in the middle along the longitudinal axis and pinned to a dish. The moist artery was photographed and, then, staining of fatty streak was carried out in accordance with the method of Esper, E., et al. (*J. Lab. Clin. Med.,* 121, 103–110(1993)) as follows.

A part of the incised main artery was washed three times by 2 min. with anhydrous propylene glycol and stained for 30 min. with a saturated solution of Oil Red O (ORO, Sigma Co.) dissolved in propylene glycol. Thereafter, the artery was washed twice by 3 min. with 85% propylene glycol to remove remaining staining solution and, then washed with physical saline. The artery was photographed and the photograph was traced. The area of stained region (fatty streak region) was determined with an image analyzer (LEICA, Q-600, Germany) and its proportion (%) to the total arterial area was calculated.

On the other hand, the other part of the main artery was stained in accordance with hematoxylin-eosin (H&E) and Masson's trichrome staining methods and observed under a microscope to confirm whether the macrophage-lipid complexes were accumulated in the intima, internus, elastic lamina and media.

Further, blood samples were taken from the rabbits and total cholesterol and triglyceride levels were determined in accordance with the same procedure in Example 4.

The result is shown in Table V.

TABLE V

| Dietary Group | Total cholesterol (mg/dl) | Triglyceride (mg/dl) | M-L* complex area (%) |
| --- | --- | --- | --- |
| Control group | 1143 | 56 | 35 |
| 1 mg/kg Lovastatin ® group | 1210 | 66 | 5 |
| 0.1% naringin group | 1367 | 72 | 12 |
| 0.1% naringenin group | 1350 | 70 | 13 |

*M-L complex: Macrophage-lipid complex

As can be seen from Table V, the area of macrophage-lipid complex accumulated on the arterial endothelium decreased significantly in the 1 mg/kg Lovastatin®, 0.1% naringin and 0.1% naringenin groups, as compared to the control group. Accordingly, it has been confirmed that naringin and naringenin inhibit the accumulation of macrophage-lipid complex on the arterial endothelium. In particular, it is remarkable that the inhibitory activity of naringin and naringenin on the accumulation of macrophage-lipid complex was exhibited under the blood cholesterol levels above 1,100 mg/dl, which are much higher than that of normal rabbit, i.e., about 50 mg/dl. This result suggests that there may be a novel mechanism for preventing the onset of atherosclerosis, which is different from the blocking of cholesterol synthesis by a HMG-CoA reductase inhibitor, blocking of cholesterol absorption by an ACAT inhibitor, or blocking of cholesterol transfer by a CETP inhibitor.

Figure 1A:
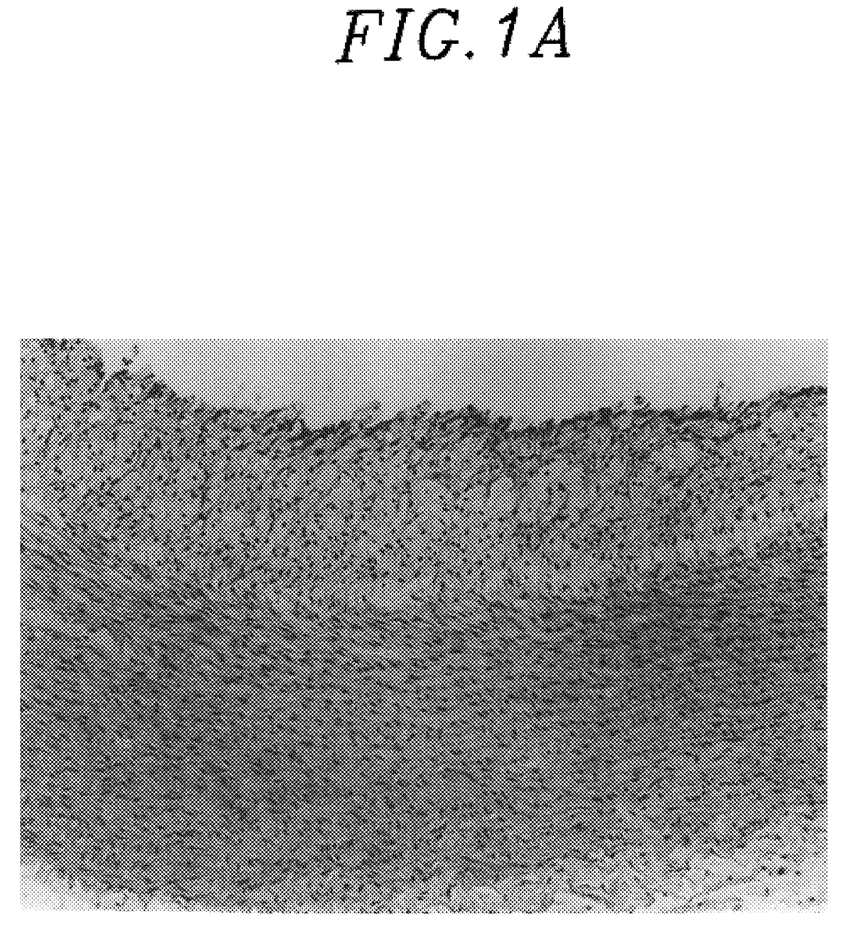
Figure 1B:
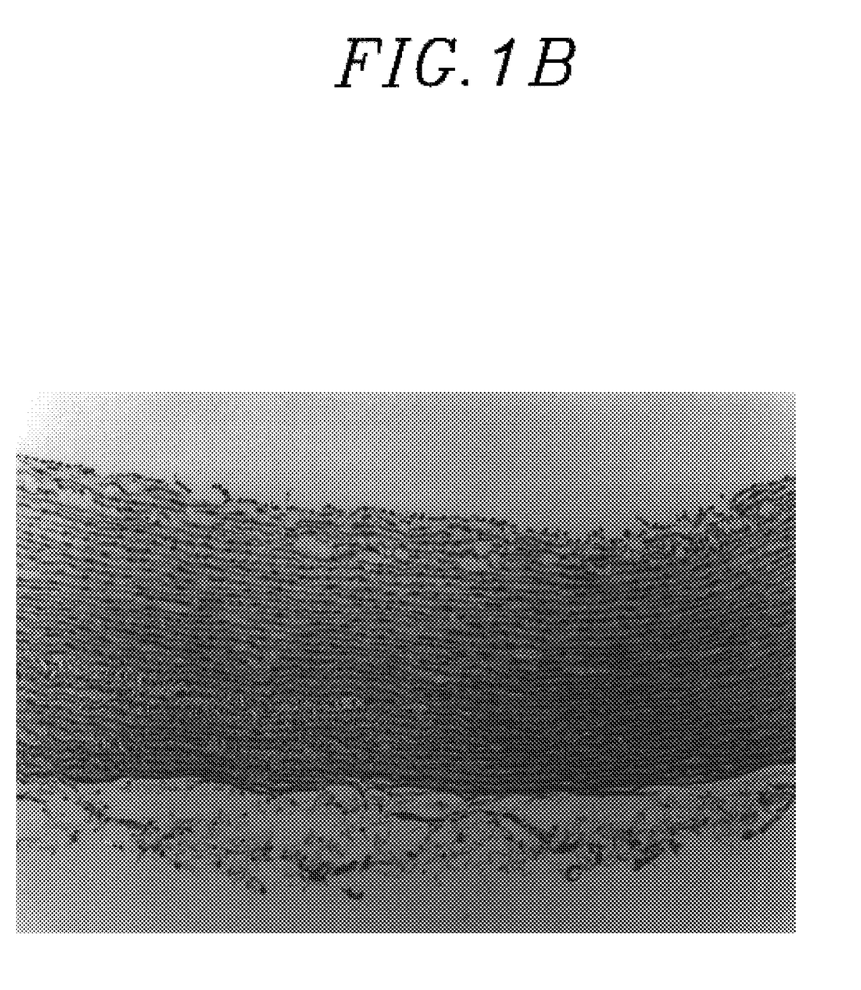
Figure 1C:
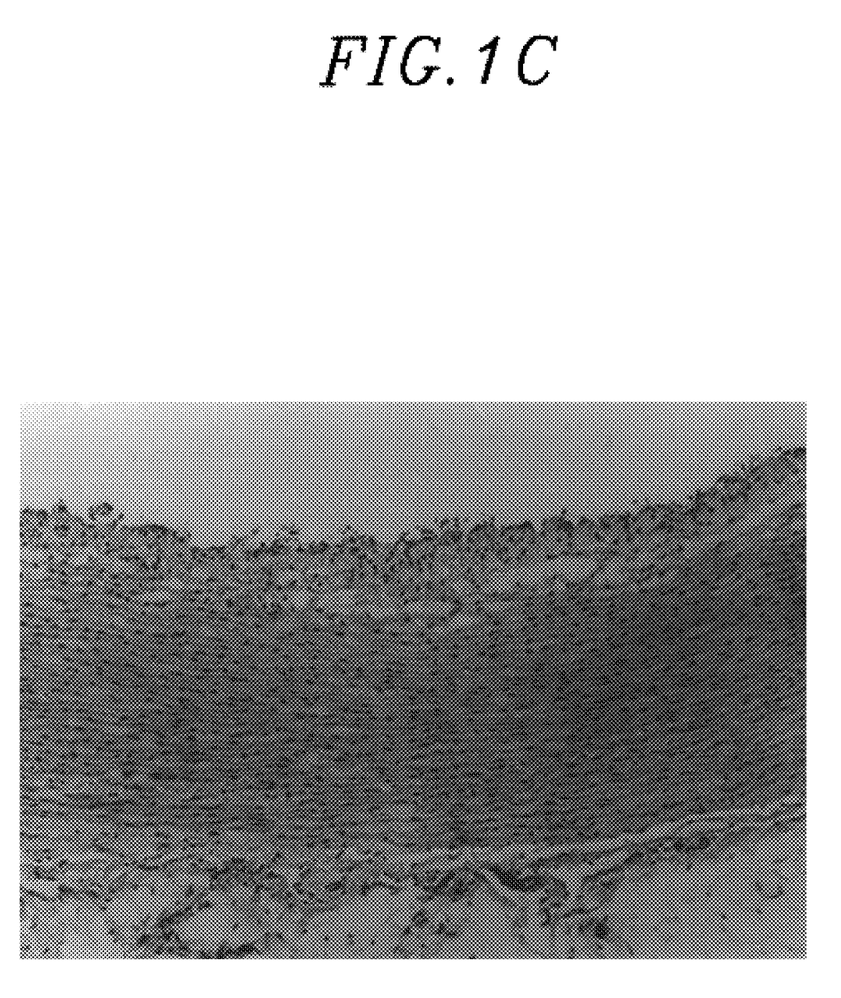

FIGS. 1A, 1B and 1C show the arteries of the rabbits administered with 1% cholesterol (control group); 1% cholesterol plus 1 mg/kg Lovastatin® (comparative group); and 1% cholesterol plus 0.1% naringin, respectively. As shown in FIGS. 1A, 1B and 1C, a thick layer of macrophage-lipid complex was observed on the arterial endothelium of the rabbit administered with 1% cholesterol, while no or very thin layers of macrophage-lipid complex were observed on the arterial endotheliums of the rabbits administered with 1% cholesterol plus 1 mg/kg Lovastatin®, and 1% cholesterol plus 0.1% naringin, respectively.

Accordingly, it has been concluded that naringin and naringenin strongly inhibit the accumulation of macrophage-lipid complex on the arterial endothelium.

EXAMPLE 7

Prevention of Hepatic Diseases by Naringin (Step 1) Administration of Naringin to Rats 20 four-week-old Sprague-Dawley rats (Taihan laboratory animal center, Korea) each weighing about 90 to 110 g were evenly divided into two dietary groups by a randomized block design. The rats of the two groups were fed with two different high-cholesterol diets, i.e., AIN-76 laboratory animal diet (ICN Biochemicals, Cleveland, Ohio, U.S.A.) containing 1% cholesterol (Control group), and 1% cholesterol plus 0.02% naringin, respectively. The compositions of the diets fed to the two groups are shown in Table VI.

TABLE VI

| Dietary group Ingredients | Control group | Naringin group |
|---|---|---|
| Casein | 20 | 20 |
| D,L-methionine | 0.3 | 0.3 |
| Corn starch | 15 | 15 |
| Sucrose | 39 | 38.98 |
| Cellulose powder*[1] | 5 | 5 |
| Mineral mixture*[1] | 3.5 | 3.5 |
| Vitamin mixture*[1] | 1 | 1 |
| Choline bitartrate | 0.2 | 0.2 |
| Fat | 15 | 15 |
| Cholesterol | 1 | 1 |
| Naringin*[2] | — | 0.02 |
| Total | 100 | 100 |

*[1]Purchased from TEKLAD premier Co. (Madison, WI, U.S.A.)
*[2]Purchased from Sigma Chemical Co. (St. Louis, Mo, U.S.A.)

The rats were allowed to feed freely on the specified diet together with water for six weeks, the ingestion amount was recorded daily and the rats were weighed every 7 days, and then the record was analyzed. All rats showed a normal growth rate and there was observed no significant difference among the two groups in terms of the feed ingestion amount and the weight gain.

(Step 2) Determination of Serum GOT and GPT Levels

The effect of administering naringin to rats on the function of the liver was examined as follows.

Blood samples were taken from the rats of the two dietary groups and serum GOT (glutamate-oxaloacetate transaminase) and GPT (glutamate-pyruvate transaminase) levels were determined in accordance with the method of Reitman and Frankel (Reitman, S. and J. S. Frankel, *Am. J. Clin. Pathol.*, 28, 56(1956)). GOT and GPT are synthesized in the liver and heart, and released into blood stream upon the damage of these organs. Accordingly, GOT and GPT are representative markers of the liver-function and high serum GOT and GPT levels mean severe damage of the liver.

The result showed that GOT and GPT levels of naringin group were lower than those of the control group by about 30% and 10%, respectively.

(Step 3) Experiment Using Rabbits

The same procedure as in (Step 1) was repeated except that 30 three-month old New Zealand White rabbits (Yeonam Horticulture and Animal Husbandry College, Korea) each weighing about 2.5 to 2.6 kg were used in place of the rats, and the rabbits were fed for six weeks with three different diets, i.e., RC4 diet containing 1% cholesterol (Control group); 1% cholesterol plus 1 mg/kg Lovastatin® (Comparative group); and 1% cholesterol plus 0.1% naringin, respectively.

Thereafter, the livers were separated from the rabbits and the histopathological observations were carried out as follows.

The rabbits were anesthetized with an intramuscular injection of ketamine (75 mg/kg) and subjected to an abdominal incision. The color and degree of sclerosis of the liver were observed with eyes, and the liver separated from the rabbit was fixed in 10% neutral buffered formalin for more than 24 hours. The fixed liver was washed sufficiently with water, dehydrated stepwise with 70%, 80%, 90% and 100% ethanol and, then, embedded in paraffin. The embedded liver was sectioned in 4 $\mu$m thickness with a microtome and stained with hematoxylin and eosin. The stained liver specimen was made transparent with xylene, mounted with permount, and then observed under a microscope to confirm the presence of lesions.

Figure 2A:
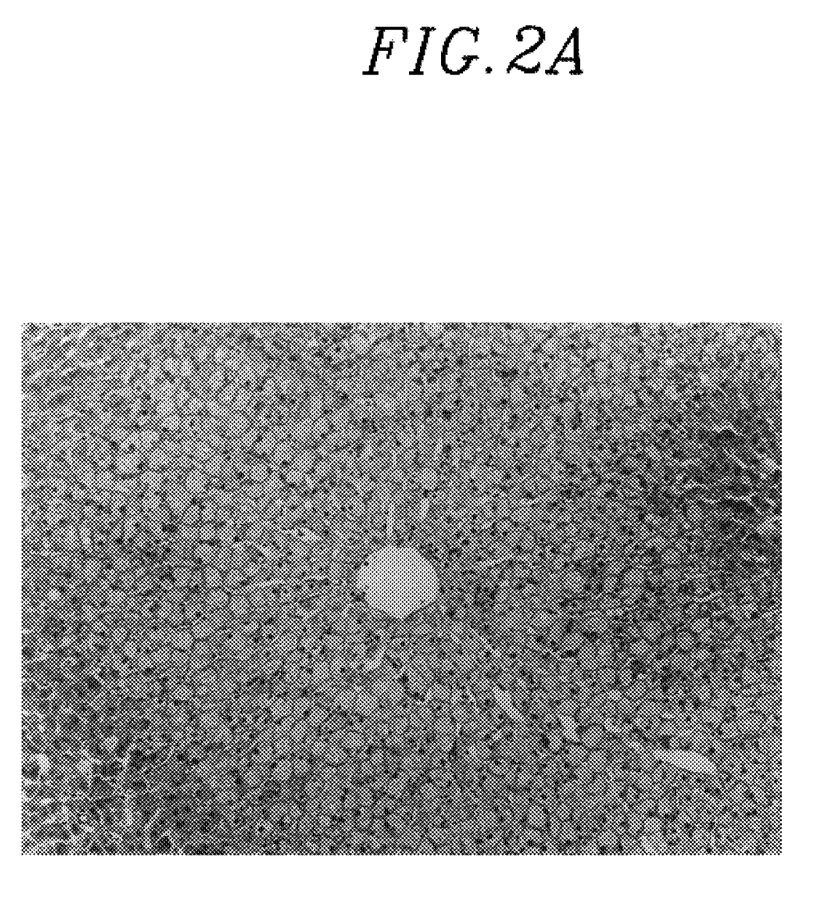
FIGS. 2A, 2B and 2C present the microscopic features of the livers of the rabbits administered with 1% cholesterol; 1% cholesterol plus 1 mg/kg Lovastatin®; and 1% cholesterol plus 0.1% naringin, respectively.
Figure 2B:
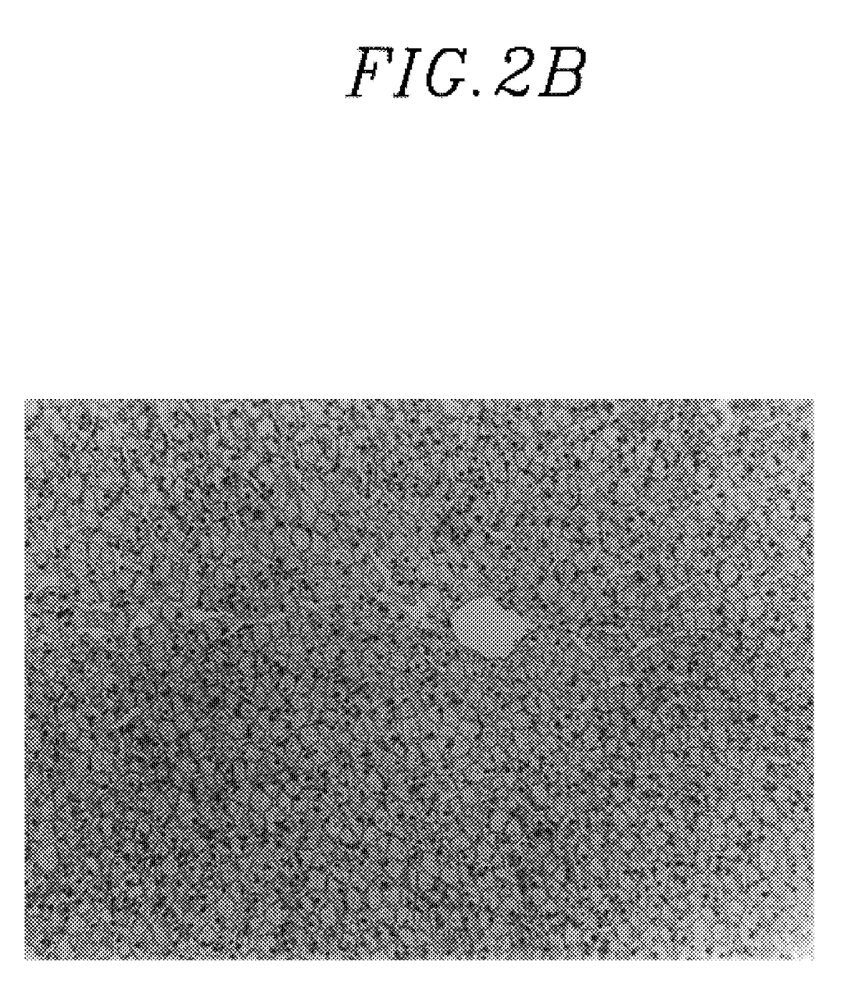
Figure 2C:
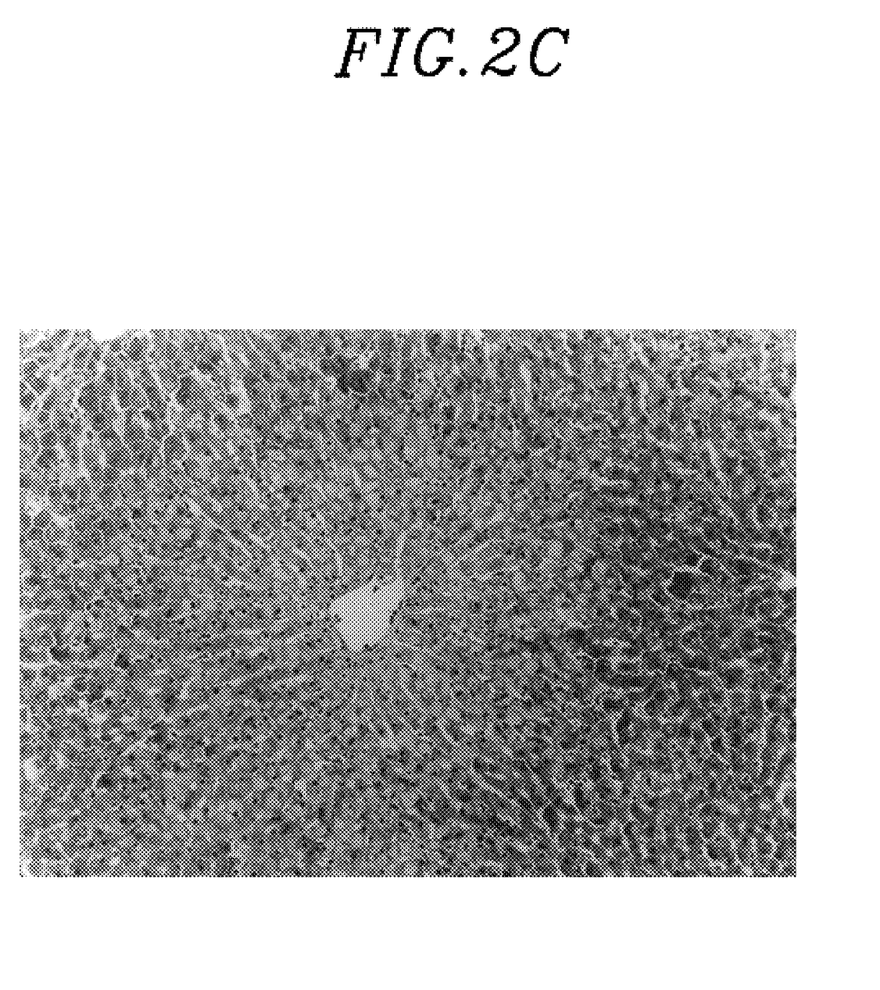

FIGS. 2A, 2B and 2C present the microscopic features of the livers of the rabbits administered with 1% cholesterol (control group), 1% cholesterol plus 1 mg/kg Lovastatin® (comparative group), and 1% cholesterol plus 0.1% naringin, respectively. As shown in FIGS. 2A and 2B, the hepatic cells of the control group and the comparative group are irregularly arranged and enlarged and a large amount of fat is deposited therein. In contrast, as shown in FIG. 2C, the hepatic cells of naringin group are normal and the deposition of fat is not observed. This result shows that naringin strongly inhibits the occurrence of fatty liver without toxic adverse effect to the hepatic cells.

(Step 4) Experiment Using Human

Naringin was orally administered to a 55-year-old man at a daily dose of 10 mg/kg for 68 days and serum GOT, GPT and $\gamma$GTP levels were determined just before the administration (day 0), and 45 and 68 days after the administration (day 45 and day 68), respectively. Consequently, serum GOT levels at day 45 and day 68 decreased by 17%, respectively, in comparison to that of day 0. Serum GPT levels at day 45 and day 68 decreased by 15% and 19%, respectively, in comparison to that of day 0. Further, serum $\gamma$GTP levels at day 45 and day 68 decreased by 25% and 51%, respectively, in comparison to that of day 0. Surprisingly, reduction of serum $\gamma$GTP level at day 68 was more than 50%, and this result suggests that naringin or naringenin has a strong liver-protective activity and preventive activity on the hepatic diseases such as hepatitis, fatty liver and alcoholic fatty liver.

On the other hand, naringin was orally administered to a 56-year-old man, who had drunk alcoholic beverages habitually in an amount of 100 cc per day, at a daily dose of 6 mg/kg for 30 days and serum γGTP level was determined just before the administration (day 0) and 30 days after the administration (day 30). Consequently, initial serum γGTP level at day 0 was 129 IU/l, while that of day 30 decreased to 69 IU/l which is within the normal range. This result demonstrates that naringin or naringenin has a high activity of preventing alcoholic fatty liver and hepatocirrhosis.

EXAMPLE 9

Foods Containing Naringin or Naringenin

Foods containing naringin or naringenin were prepared as follows.

(1) Preparation of tomato ketchup and sauce

Naringin or naringenin was added to a tomato ketchup or sauce in an amount ranging from 0.01 to 5 wt % to obtain a health-improving tomato ketchup or sauce.

(2) Preparation of wheat flour foods

Naringin or naringenin was added to a wheat flour in an amount ranging from 0.01 to 5 wt % and breads, cakes, cookies, crackers and noodles were prepared by using the mixture to obtain health-improving foods.

(3) Preparation of soups and gravies

Naringin or naringenin was added to soups and gravies in an amount ranging from 0.01 to 5 wt % to obtain health-improving soups and gravies.

(4) Preparation of ground beef

Naringin or naringenin was added to ground beef in an amount ranging from 0.01 to 5 wt % to obtain a health-improving ground beef.

(5) Preparation of dairy product

Naringin or naringenin was added to milk in an amount ranging from 0.01 to 5 wt % and various dairy products such as butter and ice cream were prepared by using the milk.

However, in case of cheese preparation, naringin or naringenin was added to the coagulated milk protein; and, in case of yogurt preparation, naringin or naringenin was added to the coagulated milk protein obtained after the fermentation.

EXAMPLE 10

Beverages Containing Naringin or Naringenin (1) Preparation of vegetable juice 200 to 10,000 mg of naringin or naringenin was added to 1000 ml of a tomato or carrot Juice to obtain a health-improving vegetable juice.

(2) Preparation of fruit juice 200 to 10,000 mg of naringin or naringenin was added to 1000 ml of an apple or grape Juice to obtain a health-improving fruit juice.

(3) Preparation of carbonated drink 200 to 10,000 mg of naringin or naringenin was added to 1000 ml of Coca-Cola® or Pepsi-Cola® to obtain a health-improving carbonated drink.

While the invention has been described with respect to the above specific embodiments, it should be recognized that various modifications and changes may be made to the invention by those skilled in the art which also fall within the scope of the invention as defined by the appended claims.

What is claimed is:

1. A method for inhibiting the activity of acyl CoA-cholesterol-o-acyltransferase (ACAT) in a mammal which comprises administering an effective amount of naringin or naringenin thereto.

2. The method of claim 1, wherein the mammal is human.

3. The method of claim 2, wherein the effective amount of naringin or naringenin ranges from 0.1 to 100 mg/kg body weight/day.

4. The method of claim 1, wherein naringin or naringenin is administered in the form of a pharmaceutical composition containing an effective amount of naringin or naringenin and a pharmaceutically acceptable carrier.

5. The method of claim 1, wherein naringin or naringenin is administered in the form of an additive or a dietary supplement in food or beverage.

6. The method of claim 5, wherein the content of naringin or naringenin in the food ranges from 0.01 to 5% by weight.

7. The method of claim 5, wherein the food is meats, chocolates, snacks, confectionery, pizza, foods made from cereal flour, gums, dairy products, soups, broths, pastes, ketchups, sauces, vitamin complexes or health foods.

8. The method of claim 7, wherein the foods made from cereal flour is breads, cakes, crackers, cookies, biscuits or noodles.

9. The method of claim 5, wherein the beverage is dairy products, vegetable juices, fruit juices, teas, alcoholic beverages or carbonated beverages.

10. The method of claim 5, wherein the content of naringin or naringenin in the beverage ranges from 200 to 10,000 mg per 1,000 ml of the beverage.

* * * * *